US009386916B2

(12) United States Patent
Predick et al.

(10) Patent No.: US 9,386,916 B2
(45) Date of Patent: Jul. 12, 2016

(54) THREE-BLADE SPINAL RETRACTOR

(71) Applicant: Life Spine, Inc., Huntley, IL (US)

(72) Inventors: Daniel Predick, Chicago, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 366 days.

(21) Appl. No.: 13/720,800

(22) Filed: Dec. 19, 2012

(65) Prior Publication Data

US 2013/0158359 A1 Jun. 20, 2013

Related U.S. Application Data

(60) Provisional application No. 61/577,857, filed on Dec. 20, 2011.

(51) Int. Cl.
*A61B 17/02* (2006.01)
*A61B 1/32* (2006.01)

(52) U.S. Cl.
CPC ............... *A61B 1/32* (2013.01); *A61B 17/0206* (2013.01)

(58) Field of Classification Search
CPC .. A61B 17/0206; A61B 1/32; A61B 17/0293; A61B 17/2833; A61B 2017/2837
USPC ................................................. 600/224, 232
See application file for complete search history.

(56) References Cited

U.S. PATENT DOCUMENTS

2005/0215866 A1* 9/2005 Kim .................. A61B 17/0293 600/233
2007/0238932 A1* 10/2007 Jones .................... A61B 17/02 600/224
2011/0130793 A1* 6/2011 Woolley et al. .............. 606/279

* cited by examiner

*Primary Examiner* — David Bates
*Assistant Examiner* — Samuel Hanna
(74) *Attorney, Agent, or Firm* — Foley & Lardner LLP

(57) ABSTRACT

A three-blade spinal retractor utilizes adjustable and lockable translating arms with angulating blades to provide triangulated medial/lateral and cephalad/caudal tissue retraction for spinal surgeries via the adjustably lockable translating arms. A medial/lateral translating arm with an angularly adjustable retraction blade co-acts and cooperates with angularly adjacent first and second cephalad/caudal translating arms with angularly adjustable retraction blades for tissue retraction and surgical site access. A plate having a medial/lateral adjustment system adjustably holds the medial/lateral translating arm, a first cephalad/caudal adjustment system adjustably holding the first cephalad/caudal translating arm and a second cephalad/caudal adjustment system adjustably holding the second cephalad/caudal translating arm. The translating arms each have a blade holder that provides angular adjustment of the blade. Angular adjustment of each blade along with medial/lateral and cephalad/caudal adjustment provides improved preciseness and stability in positioning, tissue distraction, and surgical site access.

16 Claims, 5 Drawing Sheets

THREE-BLADE SPINAL RETRACTOR

RELATED APPLICATIONS

This patent application claims the benefit of and/or priority under 35 U.S.C. §119(e) to U.S. Provisional Patent Application Ser. No. 61/577,857 filed Dec. 20, 2011, entitled "Three-Blade Spinal Retractor" the entire contents of which is specifically incorporated herein by this reference.

BACKGROUND OF THE INVENTION

1. Field of the Invention

The present invention relates to surgical devices for retracting anatomy to provide exposure of an operating site, and more particularly, to retraction apparatus providing improved access to a surgical site for a spine procedure.

2. Background

Surgical procedures typically require the use of a retractor to hold anatomies and/or tissues out of the way from the incision down to the actual surgical site. In the case of posterior spinal surgery for implanting various spine fixation components and/or other spinal orthopedic devices, it is necessary to retract different tissue types including large and strong paraspinal muscles in order to get to the actual surgical site. In order to accomplish this goal, spinal retractors have been developed that hold back the desired anatomy of a spinal surgical site and is fixed relative to the patient either directly or indirectly.

Many different types of spinal retractors are currently available many of which use retractor blades—a part of the distraction mechanism of the spinal retractor that enters the site of the incision and physically holds the anatomy apart. The retractor blades can be attached to a frame at an angle such as about 90 degrees from horizontal (i.e. generally vertical) or as to have a variable angle. However, current spinal retractors have various deficiencies. For instance, fixed angle retractor blade configurations limit flexibility of the spinal retractor, including loss of surgical site precision and overall stabilization. The variable angle retractor blade configurations lack preciseness and flexibility in retractor blade positioning.

It is therefore evident from the above that there is a need for an improved spinal retractor that can overcome the deficiencies of current spinal retractors. It is also evident from the above that there is a need for an improved spinal retractor which provides enhanced preciseness and flexibility in retractor blade positioning. It is furthermore evident that there is a need for an improved spinal retractor as aforementioned which also allows for instrument and/or component retention and positioning by the retractor blade assembly.

SUMMARY OF THE INVENTION

The present invention is a spinal retractor for spinal surgeries providing improved preciseness and stability in positioning, tissue distraction, and surgical site access. The spinal retractor utilizes adjustable and lockable translating arms with angulating blades to provide a stable surgical site finestra and the adjustable retraction of surgical site tissue.

The present spinal retractor is a three blade retractor that allows triangulated medial/lateral and cephalad/caudal tissue retraction for spinal surgeries via the adjustably lockable translating arms. A medial/lateral translating arm with an angularly adjustable retraction blade co-acts and cooperates with angularly adjacent first and second cephalad/caudal translating arms with angularly adjustable retraction blades for tissue retraction and surgical site access.

The spinal retractor includes a plate having a medial/lateral adjustment system adjustably holding the medial/lateral translating arm, a first cephalad/caudal adjustment system adjustably holding the first cephalad/caudal translating arm, and a second cephalad/caudal adjustment system adjustably holding the second cephalad/caudal translating arm. The translating arms each have a blade holder which provides angular adjustment of the blade. Angular adjustment of each blade along with medial/lateral and cephalad/caudal adjustment provides improved preciseness and stability in positioning, tissue distraction, and surgical site access.

Further aspects of the present invention will become apparent from consideration of the drawings and the following description of a preferred embodiment of the invention. A person skilled in the art will realize that other embodiments of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate a presently preferred embodiment of the invention, wherein.

Like reference numbers indicate the same or similar parts throughout the several figures.

Figure 1:
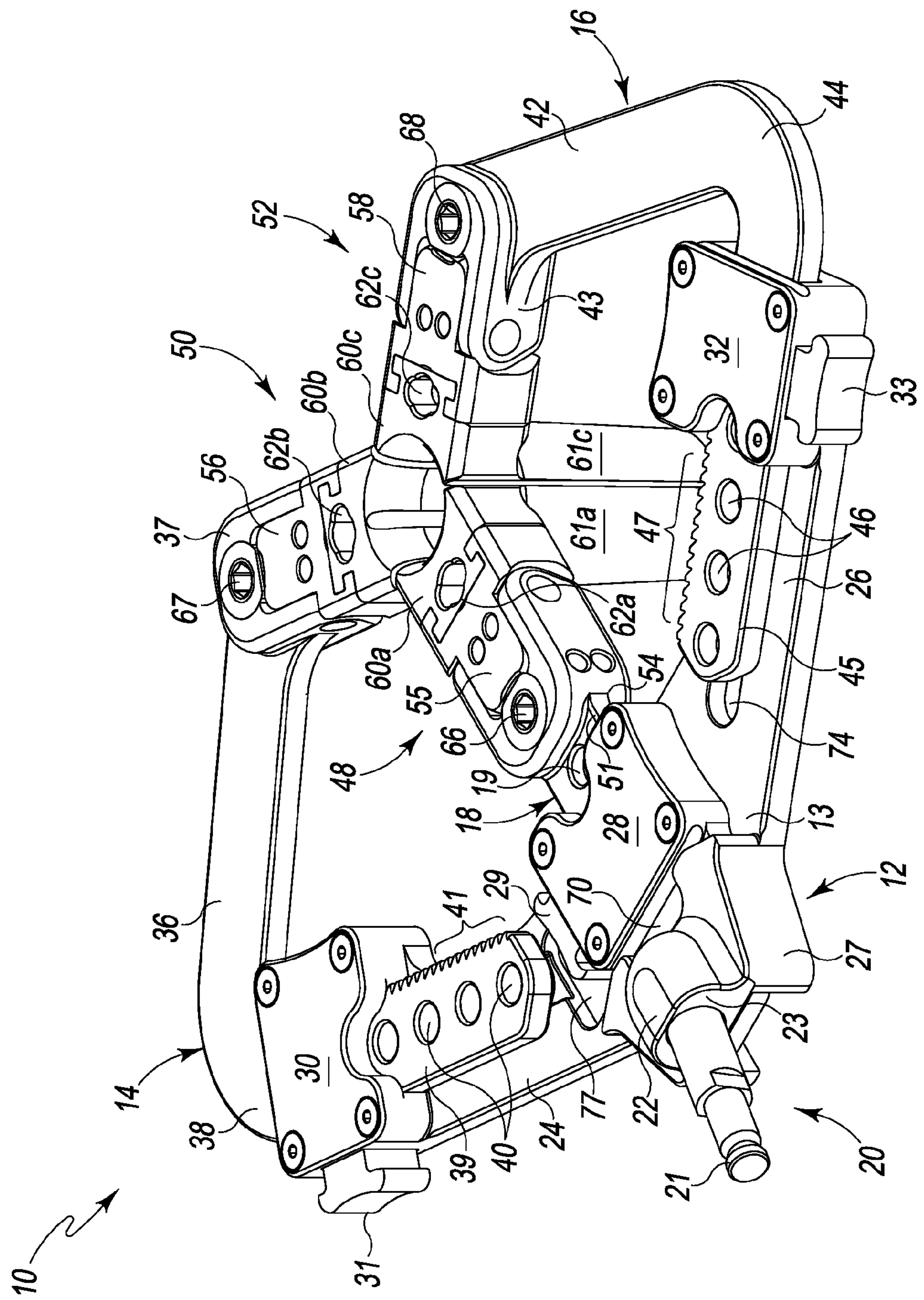
FIG. 1 is a topside view of a spinal retractor fashioned in accordance with the present principles, the spinal retractor shown in a closed position.

A description of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Reference is now made to FIGS. 1-5 which depict several views of a spinal retractor 10, fashioned in accordance with the present principles. The spinal retractor 10 is fashioned for use in anterior, posterior and lateral spinal surgeries or procedures, such as orthopedic implantation, vertebral fixation and vertebral stabilization, but may be used in other surgical procedures and orientations. The spinal retractor 10 is formed of an appropriate surgical material such as titanium, stainless steel, an alloy of same or the like.

The spinal retractor 10 has a body 12 characterized by a base, plate, platform or the like 13, a first translating arm 14 carried by the base 13 on one side thereof, a second translating arm 16 carried by the base 13 on another side thereof, wherein the sides are in the cephalad/caudal direction when the spinal retractor 10 is used, and a middle arm 18 carried by the base between the first and second translating arms 14, 16, wherein the middle arm is in the lateral/medial direction when the spinal retractor 10 is used. The base 13 further has a first side arm or wing 24 extending from a first side of the base 13 and a second side arm or wing 26 extending from a second side of the base 13. The first and second side arms 24, 26 extend generally in opposite directions relative to each other but with a slight inward angle as shown. The first and second side arms 24, 26 are in the cephalad/caudal direction when the spinal retractor 10 is used.

The spinal retractor 10 is designed to be fixed relative to a surgical site particularly, but not necessarily, to an external frame or the like (not shown) that is fixed relative to the patient. The spinal retractor 10 is also configured for rotation relative to the external frame. As such the base 13 has a boss 22 situated between opposite edges 25, 27, the boss 22 defining a face 23 from which projects a post, shaft, pole, bar, rod, stick or the like (i.e. a projection) 21. The spinal retractor 10 is connected with the external frame via the projection 21 which is received in or by a clamp, holder, receiver or the like (not shown) of the external frame. The projection 21 has a textured or keyed outer surface for engagement with the external frame, shown in the figures as radially spaced longitudinal grooves. The external surface of the projection 21 aids in positive engagement of the spinal retractor 10 with the external frame in order to fix rotational position of the spinal retractor 10 relative to the external frame.

A housing 28 is disposed on the base 13 between the first and second side arms 24, 26 and has an opening that receives the arm 18. The housing 28 cooperates with the arm 18 to provide adjustment of the arm 18 relative to the housing 28. Particularly, the arm 18 has a plurality of teeth, serrations or the like 51 on an inside edge thereof while the housing 28 includes ratchet components that cooperate with the teeth 51 of the arm 18 to provide ratcheting adjustability/translation of the arm 18 relative to the base 13. A button 29 is associated with the housing 28 and is coupled to the internal ratchet components thereof in order to allow release of the ratcheted (fixed) position of the arm 18 relative to the housing 28. In this manner, the arm 18 translates or slides in and out relative to the housing 28/base 13. Additionally, since a blade assembly 48, as described more fully below, is connected to the arm 18, the blade assembly 48 translates relative to the housing 28/base 13. This allows the blade assembly 48 to be positioned relative to the housing 28/base 13 and to the other blade assemblies 50, 52. Because of its position, the arm 18 and thus the blade assembly 48 translate or move in the medial/lateral directions when the spinal retractor 10 is in use. Position of the blade assembly 48 affects and effects retraction of tissue at the surgical site, particularly in the medial/lateral directions.

A housing 30 is disposed on an end of the first side arm 24 and has an opening that receives the first translating arm 14. The housing 30 cooperates with the first translating arm 14 to provide adjustment of the first translating arm 14 relative to the housing 30. Particularly, the first translating arm 14 has a plurality of teeth, serrations or the like 41 on an inside edge of an end 39 of the first translating arm 14 while the housing 30 includes ratchet components that cooperate with the teeth 41 of the first translating arm 14 to provide ratcheting adjustability/translation of the first translating arm 14 relative to the first side arm 24/base 13. A button 31 is associated with the housing 30 and is coupled to the internal ratchet components thereof in order to allow release of the ratcheted (fixed) position of the first translating arm 14 relative to the housing 30. In this manner, the first translating arm 14 translates or slides in and out relative to the housing 30/first side arm 24. Additionally, since the blade assembly 50, as described more fully below, is connected to the first translating arm 14, the blade assembly 50 translates relative to the housing 30/first side arm 24. This allows the blade assembly 50 to be positioned relative to the housing 30/first side arm 24 and to the other blade assemblies 48, 52.

Mention is now made to the configuration of the first translating arm 14. The first translating arm 14 is angled or bent so as to define a "boomerang" shape—i.e. an elbow or bend 38 between arm segments 36 and 39. Particularly, arm segments 36, 39 are bent to have an internal angle of less than ninety degrees (angle<90°) with around seventy degrees (70°) being shown and preferred. Other angles, of course, may be used. A head 37 is provided at an end of the arm segment 36 opposite the bend 38 and is angled so as to project essentially parallel with the arm segment 39. The head 37 holds the blade assembly 50. As seen, the first translating arm 14 is angled so that its blade assembly 50 is proximate the blade assembly 48 of the arm 18.

The first translating arm 14 moves in and out relative to the housing 30 and thus the first side arm 24 through ratcheting of the arm segment 39 with its plurality of teeth 41 cooperating with the ratchet components of the housing 30. Movement of the arm 14 moves the corresponding blade assembly 50 relative to the other blade assemblies 48, 52. Because of its position and connection with the housing 30, the first translating arm 14 translates or moves in the cephalad/caudal directions so that the blade assembly 50 also moves in the cephalad/caudal directions. Position of the blade assembly 50 affects and effects retraction of tissue at the surgical site, particularly in the cephalad/caudal directions.

A housing 32 is disposed on an end of the second side arm 26 and has an opening that receives the second translating arm 16. The housing 32 cooperates with the second translating arm 16 to provide adjustment of the second translating arm 16 relative to the housing 32. Particularly, the second translating arm 16 has a plurality of teeth, serrations or the like 47 on an inside edge of an end 45 of the second translating arm 16 while the housing 32 includes ratchet components that cooperate with the teeth 47 of the second translating arm 16 to provide ratcheting adjustability/translation of the second translating arm 16 relative to the second side arm 26/base 13. A button 32 is associated with the housing 32 and is coupled to the internal ratchet components thereof in order to allow release of the ratcheted (fixed) position of the second translating arm 16 relative to the housing 32. In this manner, the second translating arm 16 translates or slides in and out relative to the housing 32/second side arm 26. Additionally, since the blade assembly 52, as described more fully below, is connected to the second translating arm 16, the blade assembly 52 translates relative to the housing 32/second side arm 26. This allows the blade assembly 52 to be positioned relative to the housing 32/second side arm 26 and to the other blade assemblies 48, 50.

Mention is now made to the configuration of the second translating arm 16. The second translating arm 16 is angled or bent so as to define a "boomerang" shape—i.e. an elbow or bend 44 between arm segments 42 and 45. Particularly, arm segments 42, 45 are bent to have an internal angle of less than ninety degrees (angle<90°) with around seventy degrees (70°) being shown and preferred. Other angles, of course, may be used. A head 43 is provided at an end of the arm segment 42 opposite the bend 44 and is angled so as to project essentially parallel with the arm segment 45. The head 43 holds the blade assembly 52. As seen, the second translating arm 16 is angled so that its blade assembly 52 is proximate the blade assembly 48 of the arm 18.

The second translating arm 16 moves in and out relative to the housing 32 and thus the second side arm 26 through ratcheting of the arm segment 45 with its plurality of teeth 47 cooperating with the ratchet components of the housing 32. Movement of the arm 16 moves the corresponding blade assembly 52 relative to the other blade assemblies 48, 50. Because of its position and connection with the housing 32, the second translating arm 16 translates or moves in the cephalad/caudal directions so that the blade assembly 52 also moves in the cephalad/caudal directions. Position of the blade assembly 52 affects and effects retraction of tissue at the surgical site, particularly in the cephalad/caudal directions.

Ratcheting adjustment of the arm 18 and of the first and second translating arms 14, 16 (and thus adjustment of the blade assemblies 48, 50, 52) may be accomplished manually but are preferably adjusted via one or more surgical instruments or tools. As such, the arms 18, 24, 26 and the base 13 are configured to allow manipulation of the arms 18, 24, 26 by a surgical instrument or tool (not shown).

Figure 4:
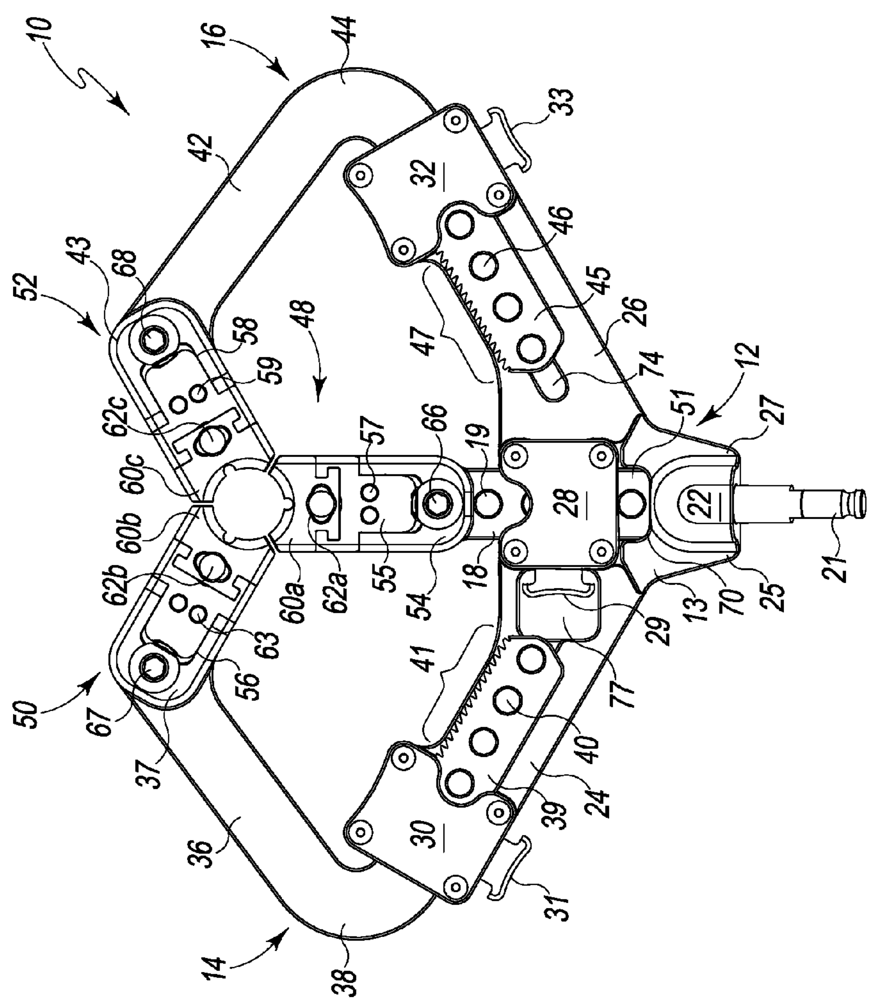
FIG. 4 is a top plan view of the spinal retractor of FIG. 1 in a closed position.

As best seen in FIGS. 1 and 4, the arm 18 has a series of holes 19 that extend along its longitudinal length. The base 13 has a slot 70 that extends through the housing 28 and which is sized to receive the arm 18. The arm 18 thus translates within the slot 70. One or more holes 19 of the arm 18 accepts a surgical instrument, tool and/or instrument/tool portion to manually move the arm 18 within the slot 70 and in conjunction/cooperation with the ratcheting housing 28. As should be appreciated, the ratcheting housing 28 allows incremental locking movement of the arm 18 in one direction while prohibiting movement in an opposite direction without the release thereof. In the case of arm 18, the arm 18 incrementally locks in a direction toward the base 13 in order to hold tissue by the blade assembly 48 in the medial/lateral direction. This allows the surgeon to incrementally manipulate the blade assembly 48 and thus the amount of tissue retraction by the blade assembly 48. Release is accomplished by the button/ratchet release system 29 associated with the housing/ratchet system 28. As best seen in FIG. 4, the button 29 extends from the housing 28 into a configured notch or recess 77 in the first side arm 24. Recessing the button 29 helps to prevent accidental activation and thus release of tissue retraction.

Figure 3:
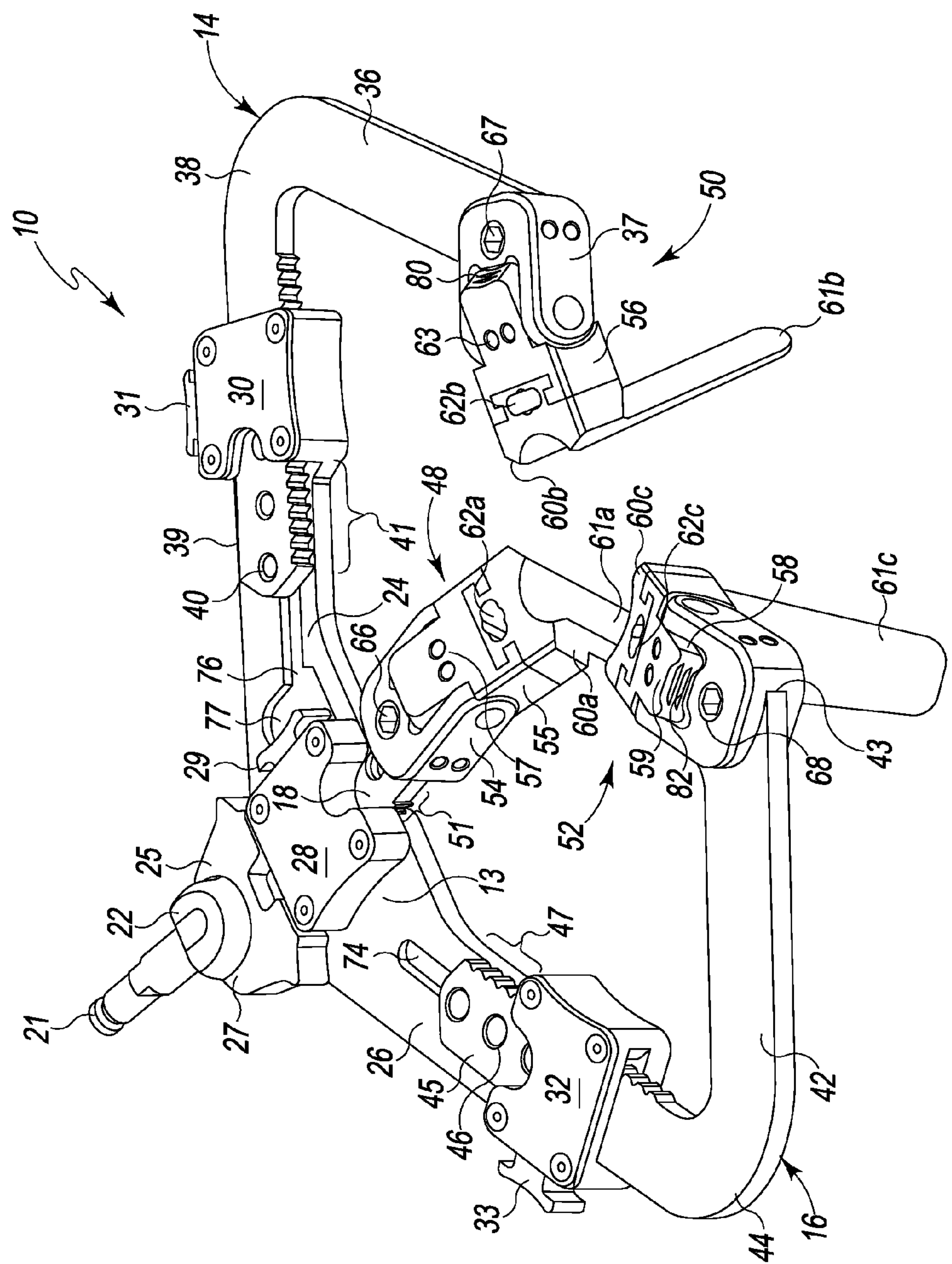
FIG. 3 is another topside view of the spinal retractor of FIG. 1 in an open position.

As best seen in FIGS. 1, 3 and 4, the first translating arm 14 has a series of holes 40 that extend along a length of the end segment 39. In conjunction therewith, the first side arm 24 of the base 13 has a slot 76 that extends from the configured recess 77 into the housing 30. The slot 76 is sized both in width and length to fit under the arm segment 39 and particularly under the holes 40. One or more holes 40 of the first translating arm 14 accepts a surgical instrument, tool and/or instrument/tool portion to manually move the arm 14 over the slot 76 and in conjunction/cooperation with the ratcheting housing 30. As should be appreciated, the ratcheting housing 30 allows incremental locking movement of the arm 14 in one direction while prohibiting movement in an opposite direction without the release thereof. In the case of the first translating arm 14, the arm 14 incrementally locks in a direction along the longitudinal length of the first side arm 24 inwardly toward the base 13 in order to hold tissue by the blade assembly 50 in the cephalad/caudal direction. This allows the surgeon to incrementally manipulate the blade assembly 50 and thus the amount of tissue retraction by the blade assembly 50. Release is accomplished by the button/ratchet release system 31 associated with the housing/ratchet system 30. The button 31 extends outward from the housing 30 helping to prevent accidental activation and thus release of tissue retraction.

As best seen in FIGS. 1, 3 and 4, the second translating arm 16 has a series of holes 46 that extend along a length of the end segment 45. In conjunction therewith, the second side arm 26 of the base 13 has a slot 74 that extends from proximate an end of the second side arm 26 near the base 13 and into the housing 32. The slot 74 is sized both in width and length to fit under the arm segment 45 and particularly under the holes 46. One or more holes 46 of the second translating arm 16 accepts a surgical instrument, tool and/or instrument/tool portion to manually move the arm 16 over the slot 74 and in conjunction/cooperation with the ratcheting housing 32. As should be appreciated, the ratcheting housing 32 allows incremental locking movement of the arm 16 in one direction while prohibiting movement in an opposite direction without the release thereof. In the case of the second translating arm 16, the arm 16 incrementally locks in a direction along the longitudinal length of the second side arm 26 inwardly toward the base 13 in order to hold tissue by the blade assembly 52 in the cephalad/caudal direction. This allows the surgeon to incrementally manipulate the blade assembly 52 and thus the amount of tissue retraction by the blade assembly 52. Release is accomplished by the button/ratchet release system 33 associated with the housing/ratchet system 32. The button 33 extends outward from the housing 32 helping to prevent accidental activation and thus release of tissue retraction.

Figure 2:
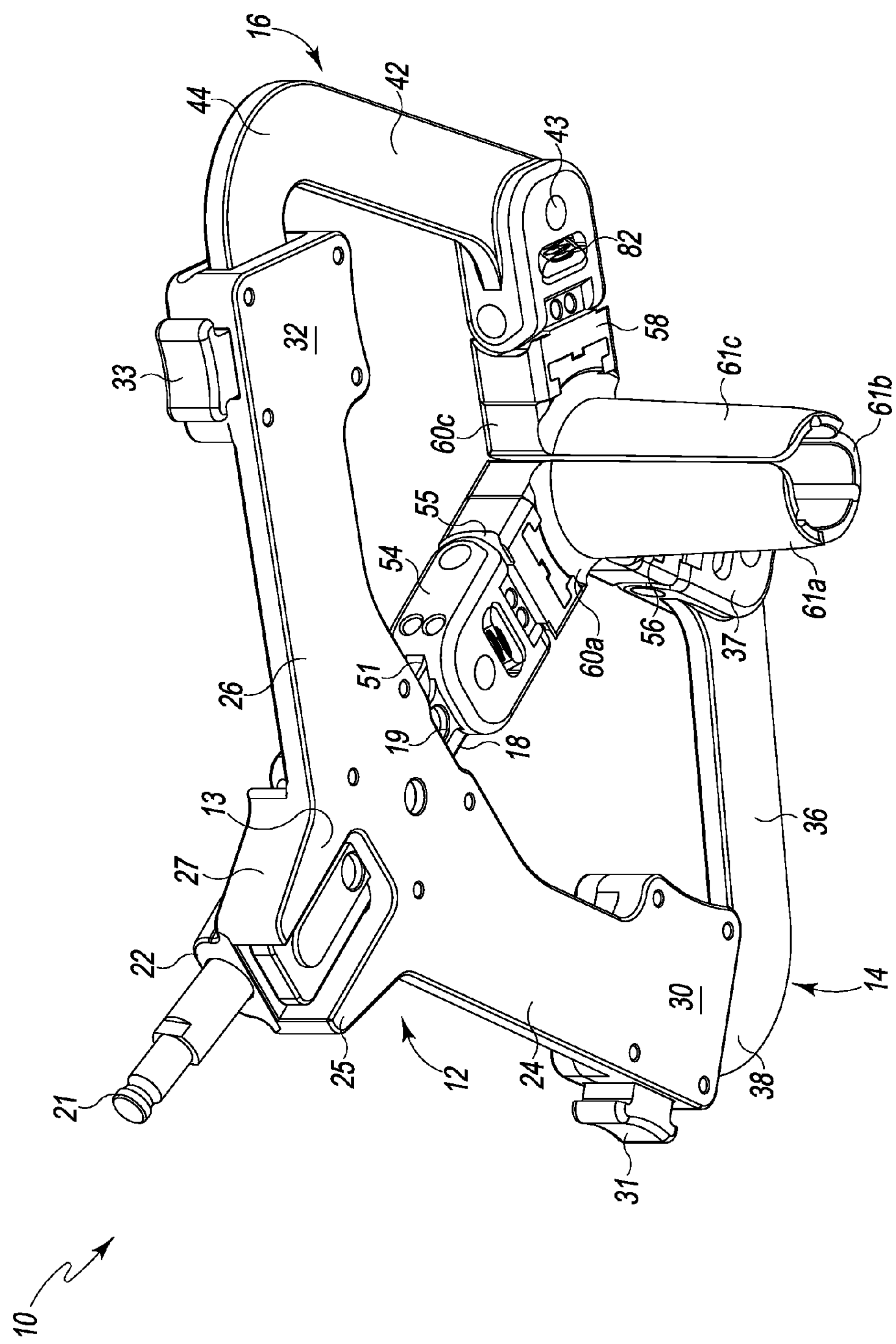
FIG. 2 is an underside view of the spinal retractor of FIG. 1 shown in a closed position.

As seen in the figures each arm 18, 14 and 16 has a respective blade assembly 48, 50, 52 for holding and retracting tissue during spinal surgery. The blade assembly 48 includes a head 54 which pivotally retains a blade holder 57 via an angulation system controlled by a set screw 66, the head 54 holding a blade 60*a*. The blade assembly 50 includes the head 37 which pivotally retains a blade holder 56 via an angulation system controlled by a set screw 67, the head 37 holding a blade 60*b*. The blade assembly 52 includes the head 43 which pivotally retains a blade holder 58 via an angulation system controlled by a set screw 68, the head 43 holding a blade 60*c*. The blades 60*a*, 60*b* and 60*c* are preferably, and as shown, identical. While each blade assembly 48, 50, 52 is identical, one or more blade assembly may be different as desired. However, in the preferred embodiment as shown, the three blade assemblies forming a triangular blade assemblage, are identical and fashioned in accordance with the present principles. Therefore, description of one blade assembly of the blade assemblies 48, 50, 52 describes the others of the blade assemblies 48, 50, 52. Moreover, the description of one blade 60*a*, 60*b*, 60*c* of the blade assemblies 48, 50, 52 describes the others of the blades 60*a*, 60*b*, 60*c*. In general, the blade assemblies 48, 50, 52 are each designed for up/down or posterior/anterior translation or angulation. In FIGS. 1, 2 and 4, the blade assemblies 48, 50, 52 are in a 0° or non-angulated position as well as in an un-retracted position. In FIG. 3, the blade assemblies 48, 50, 52 are in a downwardly angled position (an angle downwardly from 0°) as well as in a retracted position.

Figure 5:
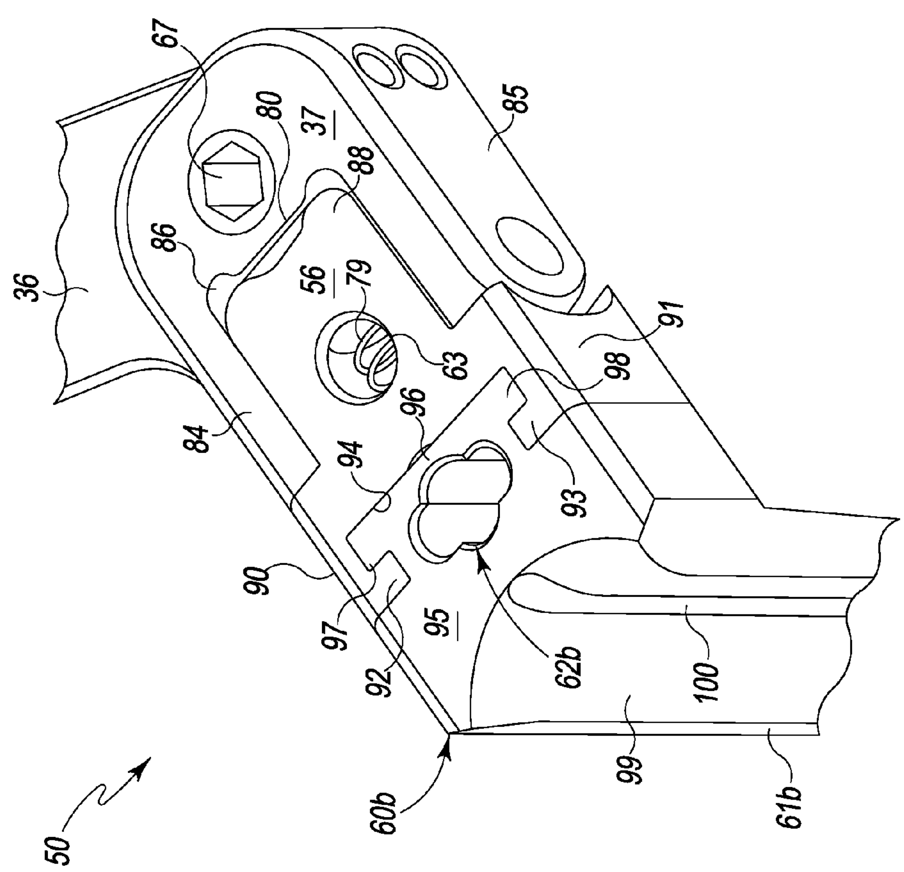
FIG. 5 is an enlarged topside view of a blade assembly on an arm of the spinal retractor of FIG. 1.

With particular reference to FIG. 5 the details of a blade assembly and blade will be described with reference to blade assembly 50. As seen, the blade holder 56 is shown in a 0° position wherein the blade 60*b* is in a full upright or vertical position. The blade holder 56 is pivotally coupled to the head 37. Particularly, an end or tongue 88 of the blade holder 56 is received within a cutout 86 of the head 37 and pivotally connected at sides thereof to arms 84 and 85 of the head 37. This allows the blade holder 56 to pivot relative to the head 37. The blade holder 56 and the head 37 are connected via the angulation adjustment system 63 which includes a worm gear system driven by the hex nut 67. Particularly (and in conjunction with FIG. 3) the hex nut 67 is externally threaded to mesh with screw serrations 80 on an end of the blade holder 56. As the hex nut 67 is rotated clockwise or counterclockwise the blade holder 56 will angulate or pivot up and down. As the blade holder 56 angulates or pivots downward, the spade portion 61*b* of the blade 60*b* moves outwardly (medially or laterally) to effect splaying of the tissue. As seen in FIG. 3, the blade holder 58 includes screw serrations 82 on an end thereof as part of its angulation adjustment system 59.

The blade holder 56 has first and second side arms 90, 91 that define a configured notch 94 that is adapted to receive a configured flange 96 of a head 95 of the blade 60*b*. The blade holder 56 and the blade 60*b* are configured to allow the blade 60*b* to be positively received and held, removed and replaced. Inwardly projecting ends 92, 93 of the first and second side arms 90, 91 define a confined slot for receipt and retention of the blade head 96, the blade flange 96 having lips 97, 98 for complementary reception by the ends 92, 93. The blade 60*b* is thus vertically inserted into and removed from the blade holder 56.

The blade holder 56 incorporates a spring loaded detent system 79 which releasably locks the blade 60*b* into the blade holder 56. The blade 60*b* has a keyed access point 62*b* to allow both insertion of the blade 60*b* into the blade holder 56 as well as actuation of the detent system 79 in order to release the blade 60*b* from the blade holder 56.

The blade 60*b* has a tong, spade, paddle or the like 61*b* that extends transverse from the head 95. An inner surface 99 of the paddle 61*b* is curved inwardly (i.e. concave relative to the head 95). A channel 100 extends from a top of the paddle 61*b* (i.e. the top of the concavity 99) to an end of the paddle 61*b*. The channel 100 receives a shaft that permits anatomical docking of the blade to bony anatomy and/or a cannula in which lighting may be inserted to aid in intraoperative visualization. Rounded corners permit the finestra formed by the blades 60*a*, 60*b*, 60*c* to maintain the same diameter as the blades are angulated.

It should be appreciated that the present spinal retractor 10 provides a table mount connection to secure retractor position relative to the patient via the frame (table). The cephalad/caudal translating arms incrementally lock positions via ratcheting teeth within each ratchet housing and subsequently expand both soft tissue retraction by means of the blades. Each translating arm can be moved independently. The cephalad/caudal translating arms cooperate and co-act with the medial/lateral translating arm to provide a stable finestra and retraction. Thumb actuated depressors release the locked positions of the arms and thus the blades. Adjustable convergence of each translating arm 14, 16, 18 with respective blades creates an adjustable finestra to the surgical site.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spinal retractor comprising:

a plate having a medial side including a first housing including a first lock and release mechanism, a lateral side including a second housing including a second lock and release mechanism, and a central side including a third housing including a third lock and release mechanism, wherein the medial side and the lateral side extend away from opposite sides of the central side at an angle such that the medial side and the lateral side extend relative to each other at an obtuse angle;

a first arm extending from the medial side of the plate and including a first arm proximal end having a plurality of locking features configured to translate within the first housing along the medial side of the plate and interlock with the first lock and release mechanism, a first arm distal end, and a first arm intermediate elongated body portion extending between the proximal and distal ends of the first arm, wherein the first arm proximal end is parallel to the first arm distal end, and wherein the distal and proximal ends of the first arm extend along parallel central axes offset from and not parallel to a central axis of the intermediate elongated body portion of the first arm;

a second arm extending from the lateral side of the plate and including a second arm proximal end having a plurality of locking features configured to translate within the second housing along the lateral side of the plate and interlock with the second lock and release mechanism, a second arm distal end, and a second arm intermediate elongated body portion extending between the proximal and distal ends of the second arm, wherein the second arm proximal end is parallel to the second arm distal end, and wherein the distal and proximal ends of the second arm extend along parallel central axes offset from and not parallel to a central axis of the intermediate elongated body portion of the second arm;

a third arm extending from the central side of the plate and including a third arm proximal end having a plurality of locking features configured to translate within the third housing along the central side and interlock with the third lock and release mechanism, a third arm distal end distal the central side of the plate, and an intermediate elongated body portion extending between the proximal and distal ends of the third arm, wherein the distal and proximal ends of the third arm are axially aligned and extend along a common central axis with the intermediate elongated body portion of the third arm;

a first blade holder pivotally connected to the first arm distal end, the first blade holder being angularly adjustable relative to the first arm and configured to receive a first retractor blade;

a second blade holder pivotally connected to the second arm distal end, the second blade holder being angularly adjustable relative to the second arm and configured to receive a second retractor blade; and a third blade holder pivotally connected to the third arm distal end, the third blade holder being angularly adjustable relative to the third arm and configured to receive a third retractor blade;

wherein the first arm is configured to translate within and be incrementally lockable within the first housing by the first lock and release mechanism independent from and in a non-simultaneous fashion relative to the second arm when the second arm is received within the second housing and relative to the third arm when the third arm is received within the third housing, wherein the second arm is configured to translate within and be incrementally lockable within the second housing by the second lock and release mechanism independent from and in a non-simultaneous fashion relative to the first arm when the first arm is received within the first housing and relative to the third arm when the third arm is received within the third housing, and wherein the third arm is configured to translate within and be incrementally lockable within the third housing by the third lock and release mechanism independent from and in a non-simultaneous fashion relative to the first arm when the first arm is received within the first housing and relative to the second arm when the second arm is received within the second housing; and wherein translation of the proximal end of each of the first , second, and third arms along the medial, lateral, and central sides, respectively, of the plate, moves the distal end of each of the first, second, and third arms toward and away from each other.

2. The spinal retractor of claim 1, wherein:

the first arm is lockable in a first translated position relative to the medial side of the plate;

the second arm is lockable in a second translated position relative to the lateral side of the plate; and the third arm is lockable in a third translated position relative to the central side of the plate.

3. The spinal retractor of claim 2, wherein:

the first blade holder is lockable in a first angular position relative to the first arm;

the second blade holder is lockable in a second angular position relative to the second arm; and the third blade holder is lockable in a third angular position relative to the third arm.

4. The spinal retractor of claim 3, further comprising:

a first retractor blade configured to be received in the first blade holder;

a second retractor blade configured to be received in the second blade holder; and a third retractor blade configured to be received in the third blade holder.

5. A spinal retractor comprising:

a plate having a projecting medial side defining a medial end, a projecting lateral side defining a lateral end, and defining a central side between the projecting medial and lateral sides, wherein the medial side and the lateral side extend away from opposite sides of the central side at an angle such that the medial and lateral sides extend relative to each other at an obtuse angle n;

a medial housing coupled to the medial end and including a first lock and release mechanism;

a lateral housing coupled to the lateral end and including a second lock and release mechanism;

a central housing coupled to the central side and including a third lock and release mechanism;

a first arm including a first arm proximal end having a plurality of locking features received in the medial housing and configured to translate within the medial housing along the medial side of the plate and interlock with the first lock and release mechanism, a first arm distal end, and a first arm intermediate elongated body portion extending between the proximal and distal ends of the first arm, wherein the first arm proximal end is parallel to the first arm distal end, and wherein the distal and proximal ends of the first arm extend along parallel central axes offset from and not parallel to a central axis of the intermediate elongated body portion of the first arm;

a second arm including a second arm proximal end having a plurality of locking features received in the lateral housing and configured to translate within the lateral housing along the lateral side of the plate and interlock with the second lock and release mechanism, a second arm distal end, and a second arm intermediate elongated body portion extending between the proximal and distal ends of the second arm, wherein the second arm proximal end is parallel to the second arm distal end, and wherein the distal and proximal ends of the second arm extend along parallel central axes offset from and not parallel to a central axis of the intermediate elongated body portion of the second arm;

a third arm including a third arm proximal end having a plurality of locking features received in the central housing and configured to translate within the central housing along the central side of the plate and interlock with the third lock and release mechanism, a third arm distal end, and an intermediate elongated body portion extending between the proximal and distal ends of the third arm, wherein the proximal and distal ends of the third arm are axially aligned along a common central axis with the intermediate elongated body portion of the third arm;

a first blade holder pivotally coupled to the first arm distal end, the first blade holder being angularly adjustable relative to the first arm and configured to receive a first retractor blade;

a second blade holder pivotally coupled to the second arm distal end, the second blade holder being angularly adjustable relative to the second arm and configured to receive a second retractor blade; and a third blade holder pivotally coupled to the third arm distal end, the third blade holder being angularly adjustable relative to the third arm and configured to receive a third retractor blade;

wherein the first arm is configured to translate within and be incrementally lockable within the medial housing by the first lock and release mechanism independent from and in a non-simultaneous fashion relative to the second arm when the second arm is received within the lateral housing and relative to the third arm when the third arm is received within the central housing, and wherein the second arm is configured to translate within and be incrementally lockable within the lateral housing by the second lock and release mechanism independent from and in a non-simultaneous fashion relative to the first arm when the first arm is received within the medial housing and relative to the third arm when the third arm is received within the central housing, and wherein the third arm is configured to translate within and be incrementally lockable within the central housing by the third lock and release mechanism independent from and in a non-simultaneous fashion relative to the first arm when the first arm is received within the medial housing and relative to the second arm when the second arm is received within the lateral housing; and wherein translation of the proximal end of each of the first, second, and third arms along the medial, lateral and central sides, respectively, of the plate, moves the distal end of each of the first , second, and third arms toward and away from each other.

6. The spinal retractor of claim 5, wherein:

the first blade holder is lockable in a first angular position relative to the first arm;

the second blade holder is lockable in a second angular position relative to the second arm; and the third blade holder is lockable in a third angular position relative to the third arm.

7. The spinal retractor of claim 6, further comprising:

a first retractor blade configured to be received in the first blade holder;

a second retractor blade configured to be received in the second blade holder; and a third retractor blade configured to be received in the third blade holder.

8. The spinal retractor of claim 5, wherein:

the first arm has a first bend situated between the first arm proximal end and the first arm distal end thereof; and the second arm has a first bend situated between the second arm proximal end and the second arm distal end thereof.

9. A spinal retractor, comprising:

a plate including a first housing, a second housing, and a third housing, the first housing positioned at a first side of the plate and including a first lock and release mechanism, the second housing positioned at a second side of the plate and including a second lock and release mechanism, and the third housing positioned at a central portion of the plate and including a third lock and release mechanism, wherein the first and second sides extend away from opposite sides of the central portion at an angle such that the first and second sides extend relative to each other at an obtuse angle;

a first arm coupled to the plate and configured to translate relative to the plate along the first side in a first lateral direction, wherein the first arm includes a first arm proximal portion having a plurality of locking features configured to translate within the first housing and interlock with the first lock and release mechanism, a first arm distal portion, and an intermediate elongated body portion extending between the proximal and distal portions of the first arm, wherein the first arm proximal portion is parallel to the first arm distal portion, and wherein the distal and proximal portions of the first arm extend along parallel central axes offset from and not parallel to a central axis of the intermediate elongated body portion of the first arm;

a second arm coupled to the plate and configured to translate relative to the plate independent from the first arm along the second side in a second lateral direction, wherein the second arm includes a second arm proximal portion having a plurality of locking features configured to translate within the second housing and interlock with the second lock and release mechanism, a second arm distal portion, and an intermediate elongated body portion extending between the proximal and distal portions of the second arm, wherein the second arm proximal portion is parallel to the second arm distal portion, and wherein the distal and proximal portions of the second arm extend along parallel central axes offset from and not parallel to a central axis of the intermediate elongated body portion of the second arm;

a third arm coupled to the plate and configured to translate relative to the plate along the central portion in a central direction, wherein the central direction defines acute angles with both the first lateral direction and the second lateral direction, wherein the third arm includes a third arm proximal portion having a plurality of locking features configured to translate within the third housing and interlock with the third lock and release mechanism, a third arm distal portion, and an intermediate elongated body portion extending between the proximal and distal portions of the third arm, wherein the distal and proximal portions of the third arm are axially aligned and extend along a common central axis of the intermediate elongated bod y portion of the third arm;

a first blade assembly pivotally coupled to the first arm distal portion and configured to retract tissue;

a second blade assembly pivotally coupled to the second arm distal portion and configured to retract tissue; and a third blade assembly pivotally coupled to the third arm distal portion and configured to retract tissue;

wherein the first arm is configured to translate within and be incrementally lockable within the first housing by the first lock and release mechanism independent from and in a non-simultaneous fashion relative to the second arm when the second arm is received within the second housing and relative to the third arm when the third arm is received within the third housing, wherein the second arm is configured to translate within and be incrementally lockable within the second housing by the second lock and release mechanism independent from and in a non-simultaneous fashion relative to the first arm when the first arm is received within the first housing and relative to the third arm when the third arm is received within the third housing, and wherein the third arm is configured to translate within and be incrementally lockable within the third housing by the third lock and release mechanism independent from and in a non-simultaneous fashion relative to the first arm when the first arm is received within the first housing and relative to the second arm when the second arm is received within the second housing; and wherein translation of the proximal portion of each of the first, second, and third arms along the first side, second side, and central portion, respectively, of the plate, moves the distal portion of each of the first, second, and third arms toward and away from each other.

10. The spinal retractor of claim 9,

Wherein the first lock and release mechanism includes a first ratcheting mechanism and the second lock and release mechanism includes a second ratcheting mechanism.

11. The spinal retractor of claim 10, wherein the first ratcheting mechanism provides incremental locking movement of the first arm relative to the plate and the second ratcheting mechanism provides incremental locking movement of the second arm relative to the plate.

12. The spinal retractor of claim 1, wherein the first arm includes a first plurality of holes and the plate includes a first slot, wherein the first plurality of holes and the first slot define a range of movement of the first arm relative to the plate when the first plurality of holes and the first slot are engaged by a tool; and wherein the second arm includes a second plurality of holes and the plate includes a second slot, wherein the second plurality of holes and the second slot define a range of movement of the second arm relative to the plate when the second plurality of holes and the second slot are engaged by the tool.

13. The spinal retractor of claim 10, wherein the first lock and release mechanism includes a first button configured to enable release of the first arm from a locked position relative to the first housing; and the second lock and release mechanism includes a second button configured to enable release of the second arm from a locked position relative to the second housing.

14. The spinal retractor of claim 1, wherein the plurality of locking features on each of the first arm, the second arm, and the third arm include at least one of a plurality of teeth or a plurality of serrations.

15. The spinal retractor of claim 5, wherein the plurality of locking features on each of the first arm, the second arm, and the third arm include at least one of a plurality of teeth or a plurality of serrations.

16. The spinal retractor of claim 9, wherein the plurality of locking features on each of the first arm, the second arm, and the third arm include at least one of a plurality of teeth or a plurality of serrations.

* * * * *